(12) United States Patent
Wada et al.

(10) Patent No.: US 6,626,883 B2
(45) Date of Patent: Sep. 30, 2003

(54) SANITARY PANTY

(75) Inventors: Mitsuhiro Wada, Kagawa (JP); Ayami Suga, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/880,257

(22) Filed: Jun. 13, 2001

(65) Prior Publication Data

US 2002/0016580 A1 Feb. 7, 2002

(30) Foreign Application Priority Data

Jun. 19, 2000 (JP) ........................................ 2000-182927

(51) Int. Cl.[7] ................................................ A61F 13/15
(52) U.S. Cl. ........................................ 604/396; 604/402
(58) Field of Search ........................ 604/385.24, 385.3, 604/393–6, 402, 385.01, 385.14; 2/400–402

(56) References Cited

U.S. PATENT DOCUMENTS

| | | | | |
|---|---|---|---|---|
| 2,705,957 A | * | 4/1955 | Mauro ........................ 604/395 |
| 2,711,735 A | * | 6/1955 | Sabo ........................... 604/396 |
| 3,232,293 A | * | 2/1966 | De Woskin .................... 2/275 |
| 3,687,141 A | * | 8/1972 | Matsuda ..................... 128/288 |
| 4,935,021 A | * | 6/1990 | Huffman et al. ......... 604/385.1 |
| 5,745,922 A | * | 5/1998 | Rajala et al. ................ 2/243.1 |
| 5,855,573 A | * | 1/1999 | Johansson ...................... 2/401 |
| 5,944,708 A | * | 8/1999 | Philpott ......................... 2/406 |

FOREIGN PATENT DOCUMENTS

| | | |
|---|---|---|
| JP | 50-2514 | 5/1948 |
| JP | 62-21324 | 2/1987 |
| JP | 07-136214 | 5/1995 |
| JP | 08-299386 | 11/1996 |

* cited by examiner

*Primary Examiner*—Weilun Lo
*Assistant Examiner*—Catharine L Anderson
(74) *Attorney, Agent, or Firm*—Darby & Darby

(57) ABSTRACT

Provided is a sanitary panty having a waist band in a waist part, leg bands in leg openings, and a napkin fitting portion in a crotch part. In a three-dimensionally shaped condition as worn, a dimensional ratio between a center front length from the crotch part to the waist part and a minimum total length from the leg opening to the waist part is in a range of 80 to 200 in the total length, as taking that the center front length is 100. In a back part, an elastic lifting member extending from the crotch part to the waist part is provided.

8 Claims, 6 Drawing Sheets

SANITARY PANTY

BACKGROUND OF THE INVENTION

1. Field of the Invention

The present invention relates generally to a sanitary panty fitted sanitary napkin on a crotch part. More particularly, the invention relates to a sanitary panty which can firmly fit and maintain the sanitary napkin to prevent shifting out of touch and hardly cause uncomfortable feeling for constraining of wearer's body.

2. Description of the Related Art

A sanitary panty is required to certainly retain a sanitary napkin loaded on a crotch part thereof in firm fitting on a crotch portion of a wearer's body and to prevent the sanitary napkin from shifting out of touch.

For this purpose, various measures have been taken. For example, in Japanese Unexamined Patent Publication (Kokai) No. Heisei 7-136214, Japanese Unexamined Patent Publication (Kokai) No. Heisei 8-299386, Japanese Unexamined Utility Model Publication (Kokai) No. Showa 62-21324 and Japanese Unexamined Utility Model Publication (Kokai) No. Showa 50-2514 and so forth, a napkin fitting cloth is provided inside of the crotch part of the panty. The front and rear edges of the napkin fitting cloth are sewn to the crotch part. In the prior art disclosed in the above-mentioned publications, the napkin fitting cloth loaded the sanitary napkin may move independently of the crotch part of the panty so that displacement of the panty per se may not directly affect to the sanitary napkin. However, it should be difficult to certainly fit the sanitary napkin on the crotch portion of the wearer's body, particularly to gluteal cleft by merely providing the napkin fitting cloth.

Therefore, there has been a proposal to provide an elastic depression means for firmly fitting the sanitary napkin on the crotch portion of the wearer's body in the sanitary panty with or without the napkin fitting cloth, as shown in FIG. 7. FIG. 7 shows an example of the sanitary panty 1 with the elastic depression means as viewed from a back part 2.

In the sanitary panty 1 shown in FIG. 7, in the back part 2, an elastic member 3 is attached to extend from a crotch part 4 to a waist part 5. Upon worn on the wearer's body, an elastic lifting force of the elastic member 3 acts on the crotch part 4 to urge the sanitary napkin onto the crotch portion of the wearer.

However, in the conventional sanitary panty 1 of this type, is so-called high-cut leg type, in which edges 6a of leg parts or leg openings 6 are located close to a waist part or upper hem 5. More specifically, when a minimum total length between the uppermost position of the edge of the leg part 6 and the waist part 5 is assumed as L2, L2 becomes less than or equal to 40% of a center front length L1. In the sanitary panty 1 of this kind, it is common to provide leg bands 7 along the edges of the leg parts 6 for elastically applying wringing force for firmly fitting both side edge portions in the width direction of the sanitary napkin to prevent side-leakage of menstrual blood through both sides of the crotch part 4.

Therefore, in the worn condition, lifting forces F1 may obliquely upward act on the crotch part 4 by the leg bands 7. These lifting forces F1 act on the crotch portion of the wearer's body. Furthermore, in the sanitary panty 1 shown in FIG. 7, as worn on the wearer's body, the leg bands 7 are extended in the extent greater than or equal to 40% to develop greater lifting forces F1. As a result, ingrowing of the leg bands 7 into the wearer's crotch portion in the leg parts 6 can be caused.

In this condition, in order to urge the center portion of the sanitary napkin in the crotch part onto vaginal cavity by the lifting force F2 of the elastic member 3 the lifting force F2 has to be much greater than the oblique lifting forces F1 to be applied by the leg bands 7. As a result, both of the lifting forces F1 and F2 are applied to the crotch portion of the wearer's body to increase amount of wringing into the crotch portion.

Also, since the center portion of the crotch part 4 is lifted upward by the lifting force F2 and the both side edges of the crotch part 4 are lifted up obliquely by the lifting forces F1, the crotch part 4 of the sanitary panty 1 tends to be collapsed (or inwardly deformed) to reduce width dimension. Therefore, collapsing force acts on the sanitary napkin in the width direction to collapse the sanitary napkin toward the center thereof to cause reduction of absorbing area for menstrual blood.

In the sanitary panty 1 of the shape shown in FIG. 7, the edge portion of the leg openings 6, such as a portion 6b close to the crotch part, for example, tends to roll up to easily propagate to the crotch part 4. When rolling up is caused in the crotch part 4, fitting condition of the sanitary napkin becomes more unstable.

SUMMARY OF THE INVENTION

An object of the present invention is to provide a sanitary panty which can fit a sanitary napkin on a crotch portion, to reduce wringing into the crotch portion with providing wearing comfort.

According to an aspect of the present invention, a sanitary panty having a waist band in a waist part, leg bands in leg openings, and a napkin fitting portion in a crotch part, wherein in a three-dimensionally shaped condition as worn, a dimensional ratio between a center front length from the crotch part to the waist part and a minimum total length from the leg opening to the waist part, as taking that the center front length is 100, is in a range of 80 to 200 in the total length, and an elastic lifting member extending from the crotch part to the waist part is provided in a back part.

In the preferred construction, an inseam dimension from center of the crotch part to the leg opening may be greater than or equal to 30 mm.

With the sanitary panty constructed as set forth above, has longer total length than the conventional one, the leg bands may not constrain a region extending from a portion close to the crotch portion to a haunch bone as in the prior art shown in FIG. 7 and, instead, are fitted on femoral region of a wearer. Accordingly, oblique lifting force by the leg bands is not applied to the crotch portion to wring into the crotch portion. Furthermore, since large lifting force by the leg bands does not act on the crotch portion, the sanitary napkin can be certainly urged onto the crotch portion by the elastic lifting member provided in the back part.

Also, in the present invention, the crotch part may be formed with a stretchable cloth which can stretch in back and forth direction, and a napkin fitting cloth may be provided inside of the crotch part. The front edge and the back edge of the napkin fitting cloth may be sewn with the crotch part in a front side sewing portion and in a back side sewing portion, and the intermediate portion thereof may be not sewn to the crotch part.

The sanitary panty according to the present invention has a long inseam dimension as 30 mm or more. Also, since the leg opening is located around the femoral region, a crotch width of the crotch part becomes wide. Accordingly, by providing the napkin fitting cloth inside of the crotch part, the sanitary napkin can be certainly held inside of the crotch part having wide width independent of the crotch part.

In the preferred construction, with taking a width dimension of the napkin fitting cloth being 100, a width dimension of the crotch part may be in a range of 125 to 1750.

Between the front side sewing portion and the back side sewing portion, a length of the napkin fitting cloth, as taking a free length of the crotch part being 100, may be in a range of 110 to 150.

With this construction, the napkin fitting cloth will not be elongated or will cause little elongation to firmly hold the sanitary napkin with the napkin fitting cloth. Furthermore, by elongating the crotch part of the panty, the napkin fitting cloth and the sanitary napkin can be certainly urged onto the crotch portion by the elastic force of the crotch part.

The crotch cloth of an stretchable cloth may be located in the crotch part, the crotch cloth may be sewn with a front part and the back part in the front side sewing portion and in the back side sewing portion, and the front side sewing portion and the back side sewing portion extend to an edge of the leg openings.

The crotch cloth of the crotch part is independent of the front and back parts, and the front and back edges of the crotch cloth are sewn to the front and back parts. Accordingly, even if rolling up is caused in the portion of the leg openings, propagation of rolling up to the crotch cloth can be prevented.

Preferably, the elastic lifting member may be joined to a back edge of the crotch cloth in the back side sewing portion.

A longitudinal modulus of the elastic lifting member may be in a range of ±10% of a longitudinal modulus of the leg band. The longitudinal modulus means {(contracting force (N)/tensile strain (%))×100}. Therefore, the unit is (N).

In the invention, the sanitary napkin on the crotch part is lifted by the elastic lifting member in the back part. It is not necessary to provide large elastic force of the elastic lifting member in comparison with the elastic force of the leg bands.

For example, the longitudinal modulus of the elastic lifting member may be in a range of 7.5 to 10N.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
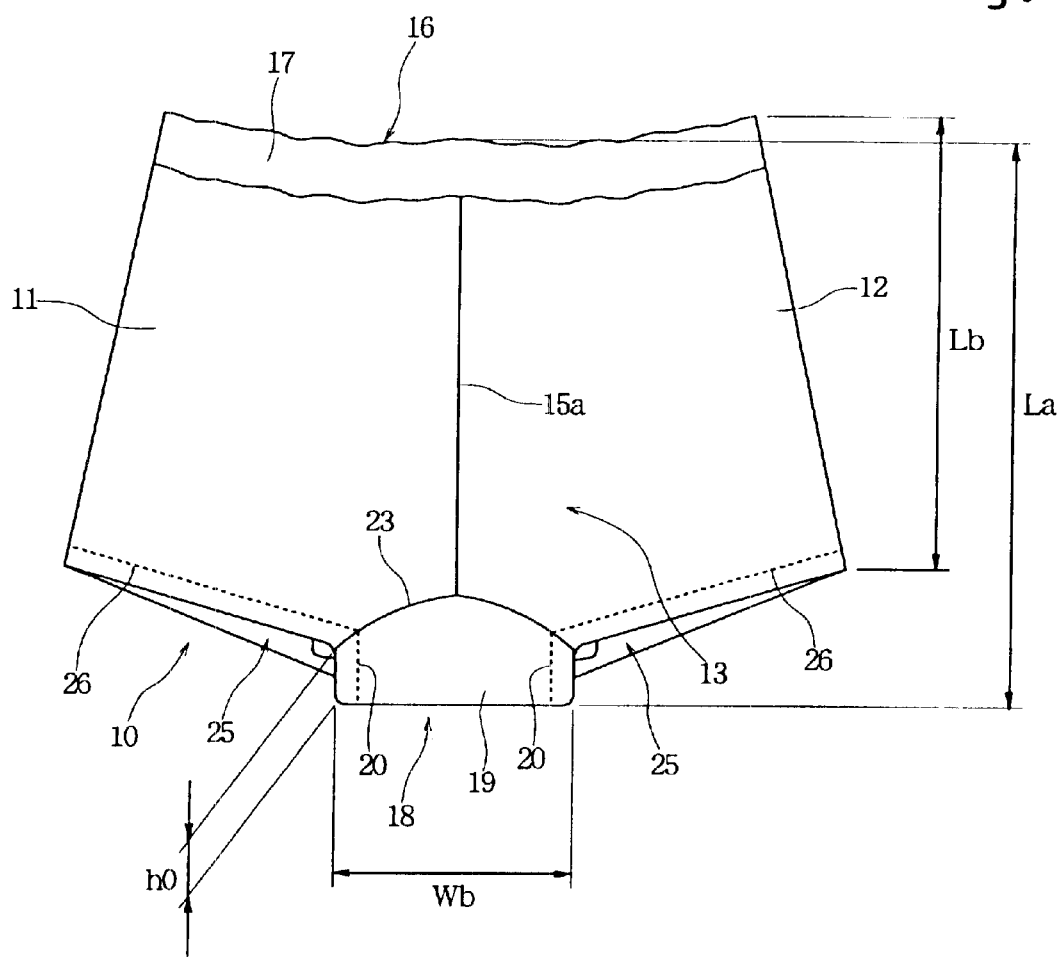
FIG. 1 is a front elevation showing one embodiment of a sanitary panty according to the present invention, which is shown in a sewn condition where a front part and a back part match with each other.
Figure 2:
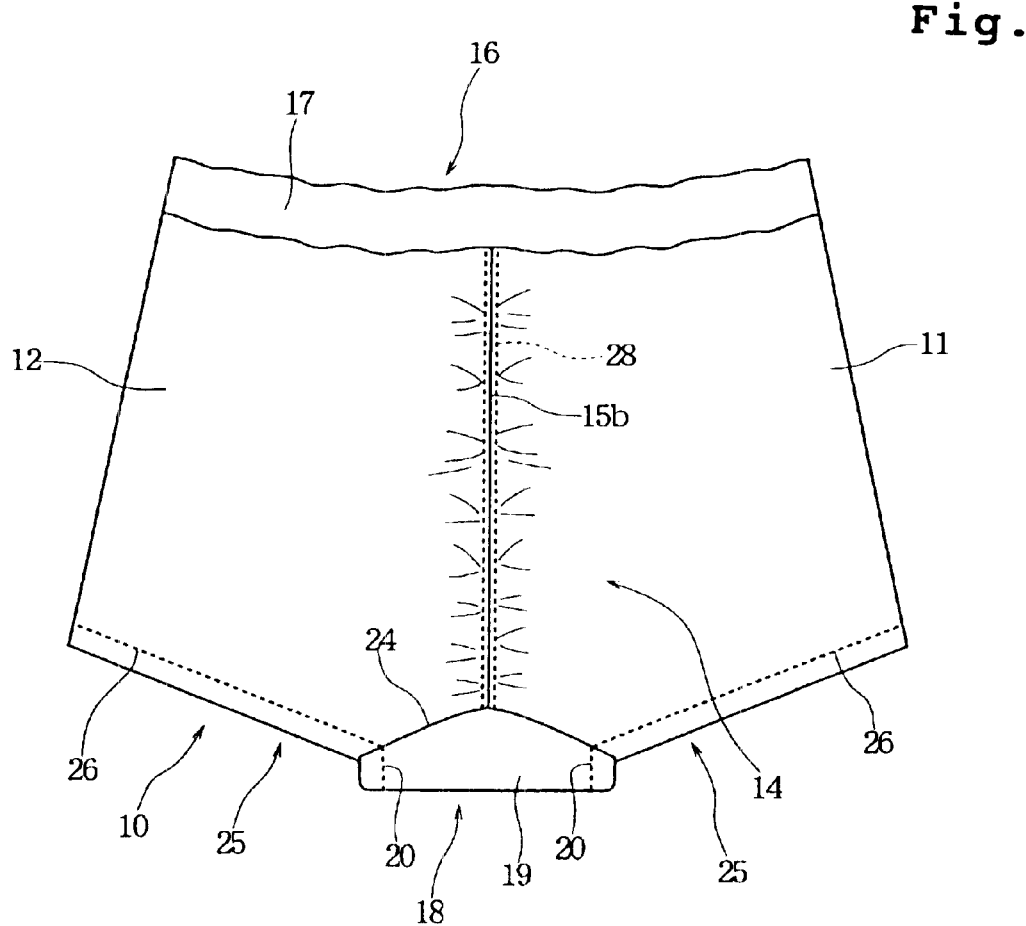
FIG. 2 is a back elevation showing one embodiment of the sanitary panty according to the present invention, which is shown in a sewn condition where a front part and a back part match with each other.
Figure 3:
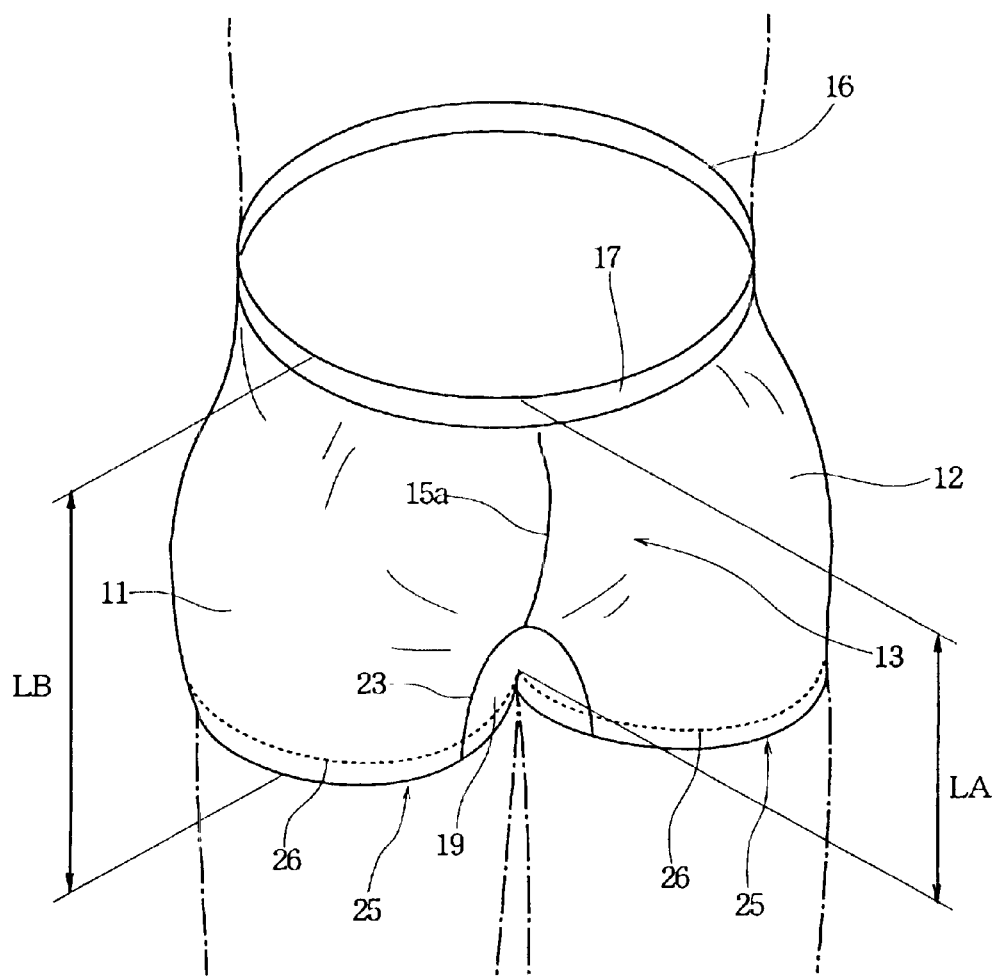
FIG. 3 is a perspective view as viewed from front side in the condition where the sanitary panty of the present invention is worn by a wearer.
Figure 4:
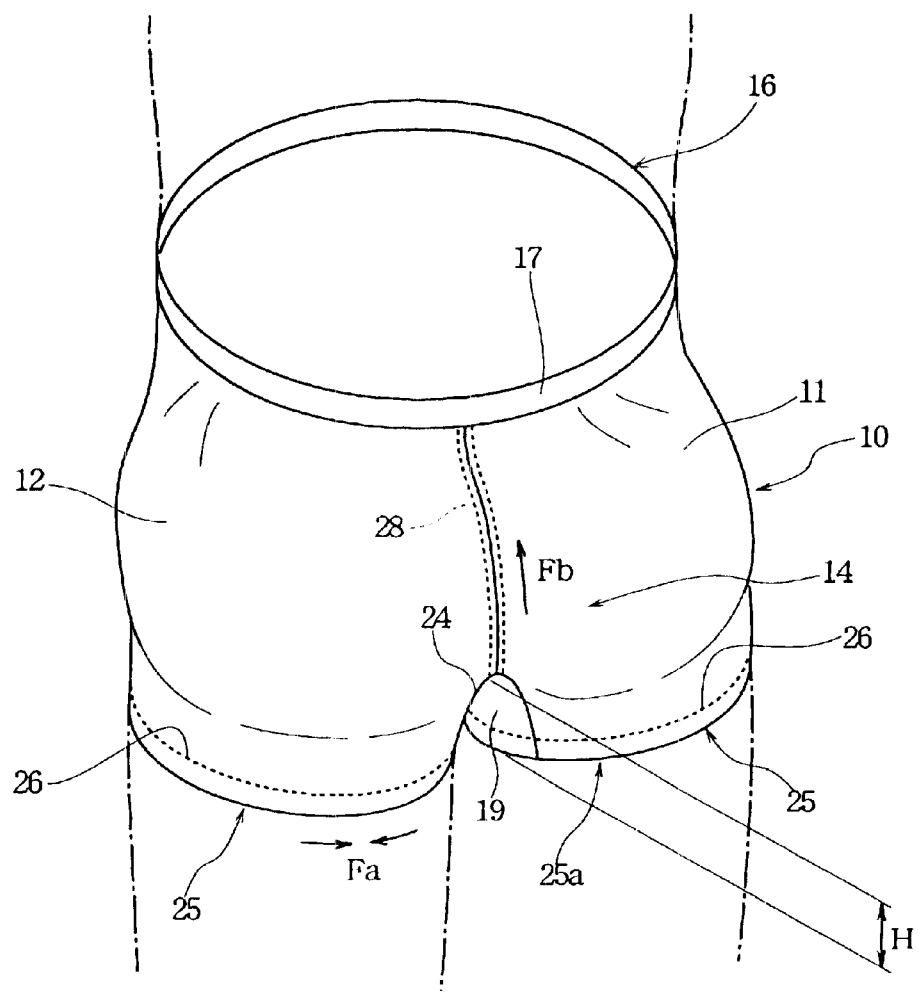
FIG. 4 is a perspective view as viewed from rear side in the condition where the sanitary panty of the present invention is worn by a wearer.
Figure 5:
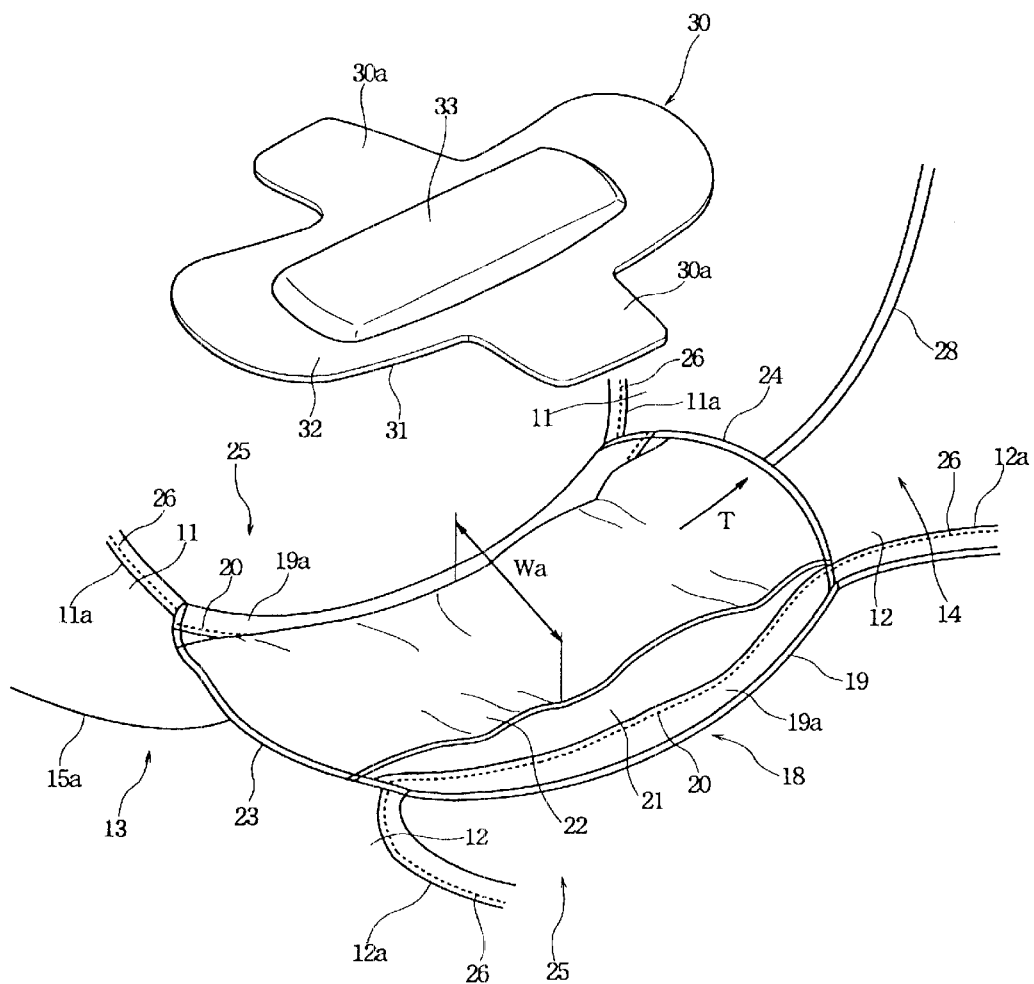
FIG. 5 is a partial perspective view of a crotch part of the sanitary panty as viewed from inside, along with a sanitary napkin to be fitted on the crotch part.
Figure 6:
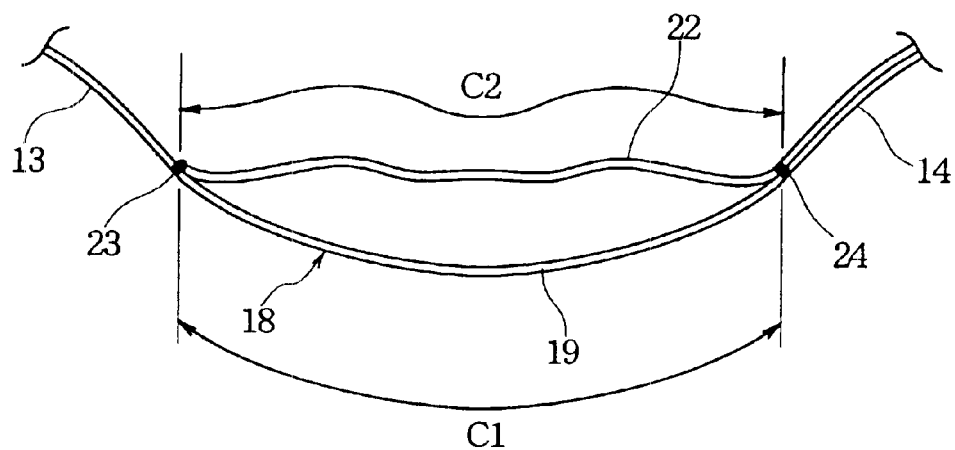
FIG. 6 is a partial side elevation of the crotch part of the sanitary panty.

FIG. 1 is a front elevation showing one embodiment of a sanitary panty according to the present invention, which is shown in a sewn condition where a front part and a back part match with each other. FIG. 2 is a back elevation showing one embodiment of the sanitary panty according to the present invention, which is shown in a sewn condition where a front part and a back part match with each other. FIG. 3 is a perspective view as viewed from front side in the condition where the sanitary panty of the present invention is worn by a wearer. FIG. 4 is a perspective view as viewed from rear side in the condition where the sanitary panty of the present invention is worn by a wearer. FIG. 5 is a partial perspective view of a crotch part of the sanitary panty as viewed from inside. And, FIG. 6 is a partial side elevation of the crotch part.

As shown in FIGS. 1 and 2, a sanitary panty 10 is formed with two hip clothes 11 and 12 which are sewn along a vertically extending sewing line 15a in a front part 13, and also sewn along a vertically extending sewing line 15b in a back part 14. The hip clothes 11 and 12 have elastic stretchability. For example, the hip clothes 11 and 12 are formed with a woven fabric of polyurethane fiber having elastic stretchability and nylon fiber having soft touch, for example. Preferred woven fabric cloth may be half tricot stitch woven fabric.

Upper portions of the front part 13 and the back part 14 form a waist part 16 (a waist part is also referred to as an upper hem). A waist band 17 extends along the waist part 16. The waist band is formed with a stretchable woven fabric of polyurethane fiber, synthetic rubber sheet, natural rubber sheet and so forth.

In a crotch part 18 of the sanitary panty 10, a crotch cloth 19 is attached. The crotch cloth 19 is also formed with a stretchable cloth of blended yarn woven fabric of polyurethane fiber and nylon fiber similar to the hip clothes 11 and 12.

As shown in FIG. 5, on inside surface of the crotch cloth 19, a waterproof sheet 21 having stretching ability and waterproofing performance, is laminated. Both side portions of the crotch cloth 19 are folded back onto the waterproof sheet 21. Folded back portions 19a are sewn with the waterproof sheet 21 along sewing lines 20. On inside of the crotch cloth 19, a napkin fitting cloth 22 is attached. The napkin fitting cloth 22 is formed with elastically stretchable woven fabric with air permeability. The napkin fitting cloth 22 is formed with non-stretchable cloth.

As shown in FIGS. 5 and 6, respective front edges of the crotch cloth 19, the waterproof sheet 21 and the napkin fitting cloth 22 are sewn to the hip clothes 11 and 12 forming the front part 13 along a front side sewing portion 23. Similarly, respective rear edges of the crotch cloth 19, the waterproof sheet 21 and the napkin fitting cloth 22 are sewn to the hip clothes 11 and 12 forming the back part 14 along a back side sewing portion 24. Between the front side sewing portion 23 and the back side sewing portion 24, the crotch cloth 19 and the napkin fitting cloth 22 are not sewn.

Between the front side sewing portion 23 and the back side sewing portion 24, a length C2 of the napkin fitting cloth 22 in back and forth direction is longer than a length C1 of the crotch cloth 19 in the back and forth direction (see FIG. 6). A dimensional ratio is, with taking the length C1 of the crotch part 19 being 100, the length C2 of the napkin fitting cloth 22 is in a range of 110 to 150 (i.e., C1:C2= 100:110–150). In practice, the length C1 is in a range of 100 mm to 200 mm and therefore the length C2 is in a range of 110 to 300 mm.

On both sides of the crotch cloth 19, leg openings or leg portions 25 are formed. As shown in FIG. 5, edge portion of the hip cloth 11 is folded back to form a folded back portion 11a having a predetermined width. Also, edge portion of the hip cloth 12 is folded back to form a folded back portion 12a having a predetermined width. The folded back portions 11a and 12a are sewn along sewing portions 26.

Since the hip clothes 11 and 12 are formed with stretchable clothes, the folded back portions 11a and 12a of the sanitary panty 10 per se serve as leg bands extending along edges of the leg openings 25. On the other hand, as shown in FIG. 5, folded back portions 19a on both side portions of the crotch cloth 19 are exposed in the leg opening and thus function as a part of the leg band.

It should be noted that while the shown embodiment of the sanitary panty 10 has the leg bands formed by folding back the hip clothes 11 and 12 and the crotch cloth 19 as set forth, it is also possible to form the leg bands with elastic bands independent of the hip clothes 11 and 12 and the crotch cloth 19 and attach these elastic bands on the peripheral edges of the leg openings 25.

On inside of the back part 14, an elastic lifting member 28 is sewn along the sewing line 15b of the hip clothes 11 and 12. The elastic lifting member 28 is formed with polyurethane band, natural rubber band, synthetic rubber band and so forth. The upper end of the elastic lifting member 18 is joined to the waist band 17 at the center portion of the back part 14. The lower end of the elastic lifting member 28 is joined to the rear edge of the crotch cloth 19 in the back side sewing portion 24.

In FIG. 5, there is shown a sanitary napkin 30 to be fitted on the napkin fitting cloth 22. The sanitary napkin 30 is a laminated body formed by sandwiching a liquid absorbing core 33 between a liquid permeable top sheet 32 and a liquid impermeable back sheet 31. On both sides of the sanitary napkin 30, wing portions 30a are formed integrally. On the rear surface of the back sheet 31, an adhesive layer for adhering to the napkin fitting cloth 22 is formed. The adhesive layer is also formed on the back surface of the wing portions 30a.

In FIGS. 3 and 4, the shown embodiment of the sanitary panty is illustrated in the condition fitted on the wearer's body or comparable three-dimensionally shaped condition. Here, the three dimensionally shaped condition may be a condition where the sanitary panty 10 is worn on a female mannequin of standard proportions. The standard proportions may have a waist size of 66 cm, and a hip size 94 cm. In the crotch portion, circumferential length in femoral region is 56.5 cm. It should be noted that when the conventional sanitary panty shown in FIG. 7 was worn on such female mannequin, a dimension around the leg opening 6 was 63.5 cm.

As shown in FIGS. 3 and 4, when the sanitary panty 10 is worn on the wearer's body or placed in comparable three-dimensionally shaped condition, the center portion of the crotch cloth 19 is lifted toward the crotch part of the wearer's body, and the leg openings 25 are fitted on the femoral regions. Namely, when the sanitary panty 10 is worn on the wearer's body or placed in comparable three-dimensionally shaped condition, a dimensional ratio between a center front length or a raise length LA from the center portion of the crotch cloth 19 to the waist part 16 and a total length LB from the edge of the leg opening 25 to the waist part 16 (at the position where the edge of the leg opening 25 is located closest to the waist part 16), is in a range of 80 to 200 in the total length LB as taking the center front length LA being 100 (i.e., LA:LB=100:80–200). For example, when the center front length LA is in a range of about 200 mm to 300 mm, the total length LB is in a range of about 160 to 600 mm.

Since the leg openings 25 are positioned around the femoral region, an inseam dimension H between the center portion of the crotch cloth 19 and the edge of the leg opening 25 on the side of the crotch part becomes large (see FIG. 4). The necessary inseam dimension H is at least 30 mm, preferably greater than or equal to 40 mm. The upper limit of the inseam dimension H is about 300 mm in the case where LB is double of LA.

On the other hand, since the inseam dimension H becomes large, the crotch width dimension Wb of the crotch cloth 19 shown in FIG. 1 relative to the width dimension Wa of the napkin fitting cloth 22 shown in FIG. 5 becomes sufficiently large.

The sanitary napkin 30 is set on the napkin fitting cloth 22 and fixed thereon by adhering the adhesive layer provided on the back sheet 31 of the sanitary napkin 30 thereto. On the other hand, when the wind portions 30a are provided with the sanitary napkin 30, the wing portions 30a are folded and wrapped on left and right side edges of the napkin fitting cloth 22. Then, adhesive layers provided on the back surfaces of the wing portions 30a adhere to the lower surface of the napkin fitting cloth 22.

The width dimension Wb of the crotch cloth 19 is greater than the width dimension Wa of the napkin fitting cloth 22, and the inseam dimension H shown in FIG. 4 becomes large in the worn condition. Therefore, even when the napkin fitting cloth 22 and the sanitary napkin 30 are shifted, the napkin fitting cloth 22 and the sanitary napkin 30 will never protrude from the leg openings 25.

On the other hand, in the condition fitted on the wearer's body, since the hip clothes 11 and 12 and the crotch cloth 19 forming the sanitary panty 10 are stretchable in back and forth direction, the napkin fitting cloth 22 and the sanitary napkin 30 are urged onto the crotch portion of the wearer's body. At this time, since the dimension C2 of the napkin fitting cloth 22 in the longitudinal direction is greater than the dimension C1 of the crotch cloth 19, the napkin fitting cloth 22 will not be elongated or elongated little. Therefore, relatively displacement between the adhesive layer provided on the back sheet of the sanitary napkin 30 and the adhesive layers on the wing portions and the napkin fitting cloth 22 will never be caused.

On the other hand, as shown in FIG. 4, the elastic lifting member 28 provided in the back part 14 is elongated vertically to generate elastic tension force Fb. At the center portion of the back part 14, the elastic tension force Fb acts in substantially straight along the medulla spinalis, gluteal cleft and the crotch portion. As shown in FIGS. 5 and 6, since the elastic lifting member 28 is joined to the center portion of the rear edge of the crotch cloth 19, large tension force T may act at the center line portion at the center in the width direction of the crotch cloth 19 positioned in the crotch portion (see FIG. 5).

By the tension force T along the center line of the crotch cloth 19, the center portion of the sanitary napkin 30 is urged onto the crotch portion of the wearer's body to tightly fit the portion of the liquid absorbing core 33 onto vaginal cavity of the wearer. Therefore, liquid absorbing performance of the sanitary napkin 30 is enhanced to hardly cause side leakage of menstrual blood.

On the other hand, while fitting force Fa by the leg bands of the leg openings 25 acts (see FIG. 4), since this fitting force Fa acts along the circumference of the femoral region, the fitting force Fa of the leg bands will not apply large pressure to the crotch portion. Accordingly, feeling of ingrowing of the crotch cloth 19 into the crotch portion can be softened. On the other hand, since elastic tension force Fb of the elastic lifting member 28 mainly acts on the sanitary napkin 30 on the crotch portion, the sanitary napkin 30 can be fitted firmly even when fitting force Fa of the leg bands is not so large. Furthermore, since it is not required to make the elastic tension force Fb of the elastic lifting member 28 excessively large, elastic tension force Fb will not cause uncomfortable constraining feeling to the wearer's body.

On the other hand, as shown in FIG. 3, in the front crotch part, the front side sewing portion 23 joining the crotch cloth 19 and the front part 13 extends to the edge portions of the leg openings 25. Similarly, as shown in FIG. 4, in the back crotch part, the back side sewing portion 24 extends to the edge portions of the leg openings 25. Therefore, for example in FIG. 4, even if rolling up is caused in the portion of the leg opening as identified by the reference numeral 25a, rolling up can be prevented by the back side sewing portion 24, and propagation of rolling up to the crotch cloth 19 can be prevented.

Next, dimension of respective portions of the sanitary panty 10 and mutual dimensional relationship therebetween will be discussed.

As shown in FIGS. 3 and 4, when the sanitary panty 10 is worn on the wearer's body or placed in comparable three-dimensionally shaped condition, a dimensional ratio between a center front length LA and a total length LB is in a range of 80 to 200 in the total length LB, as taking the center front length LA being 100. As flattened in the condition shown in FIGS. 1 and 2 and thus being not worn on the wearer's body, the following dimensional relationship is established.

As flattened in a manner shown in FIG. 1, a dimensional ratio between a center front length or a raise length La and a total length Lb as taking the center front length La being 100 is in a range of 70 to 190 in the total length Lb (i.e., La:Lb=100:70–190). The center front length La is variable depending upon elongation of the hip clothes 11 and 12, and typically in a range of 230 to 330 mm, for example. Therefore, the total length Lb is in a range of 160 to 630 mm.

The width dimension Wa of the napkin fitting cloth 22 shown in FIG. 5 substantially matches with the width dimension of the main body portion excluding the wind portions 30a of the sanitary napkin 30. Since the width dimension of the typical sanitary napkin is in a range of 40 to 70 mm, the preferred width dimension Wa of the napkin fitting cloth 22 is in a range of 40 to 80 mm. In the worn condition of the sanitary panty 10 shown in FIGS. 3 and 4, the leg openings 25 are positioned around the femoral region, the width dimension Wb of the crotch cloth 19 is longer than that of the conventional panty.

In order to attain the inseam dimension H shown in FIG. 4 greater than or equal to 30 mm, the width dimension Wb of the crotch cloth 19 has to be at least 100 mm or more. Therefore, with taking the width dimension Wa of the napkin fitting cloth 22 being 100, necessary width dimension Wb of the crotch cloth 19 is greater than or equal to 125 (i.e., Wa:Wb=100:125 or more). In the worn condition, the upper limit of the inseam dimension H is about 300 mm in the case where the total length LB is double of the center front length LA as set forth above. In this case, the necessary width dimension Wb of the crotch cloth 19 becomes 700 mm. A maximum ratio of the width dimension Wb of the crotch cloth 19 may be 1750 with taking the width dimension Wa of the napkin fitting cloth 22 being 100 (i.e., Wa:Wb=100:1750).

On the other hand, in order to attain a structure that the leg openings 25 are fitted around the femoral region in the worn condition as shown in FIGS. 4 and 5, in the sewn condition shown in FIGS. 1 and 2, the crotch cloth 19 of the predetermined width dimension Wb extends in strip form between the front part 13 and the back part 14, and both of left and right edge portions of the crotch cloth 19 forming a part of the leg openings have to be extended below the lower edges of the front part 13 and the back part 14. Accordingly, in the sewn condition shown in FIGS. 1 and 2, the lower edge of the crotch cloth 19 projects from the lower edge of the front part 13 in the extent of h0. Furthermore, the lower edge of the crotch cloth 19 extend in substantially horizontal direction.

When the inseam dimension is about 40 mm, h0 has to be about 55 mm. Preferred range of ho is in a range of 30 to 80 mm.

Embodiment

The sanitary panty shown in FIGS. 1 and 2, is produced with polyester fiber and nylon fiber. The cloth is a half tricot stitch woven cloth with nylon yarn of 79% by mass as 34 fiber strand (twist yarn) of nylon fiber of 1.3 dtex and polyurethane yarn of 21% by mass as 4 fiber strand of polyurethane fiber of 11 dtex.

Dimensions are La=260 mm, Lb=220 mm, Wb=140 mm in FIG. 1, C1=140 mm and C2=190 mm in FIG. 6.

The sanitary napkin is set on the shown embodiment of the sanitary panty and is worn by a tester. For fitting the sanitary napkin 30 on the crotch portion without causing displacement and prevent wringing force from acting on the crotch portion of the tester, elastic tension forces of the leg bands and the elastic lifting member 28 are adjusted.

Comparative Example

Figure 7:
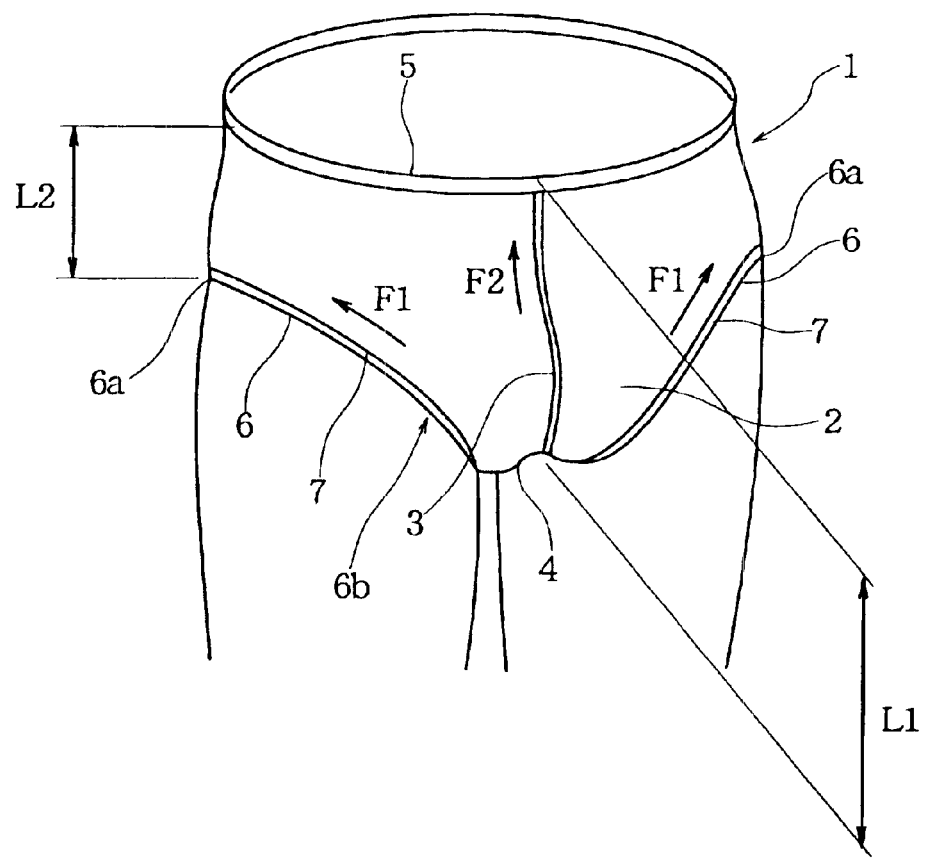
FIG. 7 is a perspective view of the conventional sanitary panty in worn condition as viewed from rear side.

A high-leg type sanitary panty shown in FIG. 7 is formed with the cloth similar to the embodiment, the center front length (corresponding to La of the embodiment) is set at 270 mm, the total length (corresponding to Lb of the embodiment) is set at 140 mm, and the width dimension of the crotch part is 70 mm.

Without providing the napkin fitting cloth in the crotch part, the elastic member 3 is provided in the back part as shown in FIG. 7.

The sanitary napkin is set on this comparative example of the sanitary panty and is worn by a tester. For fitting the sanitary napkin on the crotch portion without causing displacement, elastic tension forces of the leg bands and the elastic lifting member are adjusted.

In the embodiment and the comparative example, a relationship between an elongation percentage (strain) of the leg band and the contracting force (N) as elongated, a relationship between an elongation percentage (strain) of the elastic lifting member and the contracting force (N) as elongated, and a longitudinal modulus are shown in the following table 1. The longitudinal modulus is derived from the equation, {(contracting force (N)/tensile strain (%))×100}.

On the other hand, the elongation percentage (tensile strain) of the leg band as the embodiment and the comparative example of the sanitary panty are fitted to mannequin of standard proportions is shown in the following table 2.

TABLE 1

|  | Example | | Comparative Example | |
| --- | --- | --- | --- | --- |
| Tensile Strain (%) | 30 | 50 | 30 | 50 |
| Contracting Force of Leg Band (N) | 2.53 | 4.07 | 3.22 | 5.72 |
| Longitudinal Modulus (N) | 8.44 | 8.14 | 10.73 | 11.44 |
| Contracting Force of Elastic Lifting Member (N) | 2.47 | 4.46 | 3.69 | 6.26 |
| Longitudinal Modulus (N) | 8.25 | 8.91 | 12.31 | 12.52 |

TABLE 2

| Example | 13% |
| --- | --- |
| Comparative Example | 42.8% |

Evaluation

In the conventional sanitary panty (comparative example) shown in FIG. 7, displacement of the sanitary napkin fitted on the crotch part will be caused unless significantly large fitting force is provided for the leg band. Accordingly, as shown in the foregoing table 1, it is required to use the leg band having large longitudinal modulus. Furthermore, as shown in the table 2, elongation percentage of the leg band as worn is quite large as 42.8%. When the leg band having the longitudinal modulus shown in table 1 is used in the foregoing elongation percentage shown in the table 2, quite large fitting force of the leg band can be applied to the crotch portion to cause wringing. Also, since the large fitting force of the leg band is applied to the crotch portion, the elastic tension force of the elastic lifting member for urging the center portion of the sanitary napkin toward vaginal cavity has to be significantly large to overcome the fitting force of the leg band.

Therefore, as shown in table 1, in the comparative example, the elastic lifting member having large longitudinal modulus greater than or equal to 12.3 (N) is required. The longitudinal modulus of the elastic lifting member has to be greater than the longitudinal modulus of the leg band in the extent of 20% or more.

In contrast to this, in the shown embodiment, since the leg bands are positioned around the femoral region, elongation percentage of the leg band as worn is about 13% as shown in the table 2. On the other hand, the longitudinal modulus of the leg band is 8.44 (N) or 8.14 (N), which is much smaller than that in the comparative example. Therefore, the pressure to be exerted to the wearer's body from the leg band becomes quite small.

Also, since the leg band will never wring into the crotch portion, it becomes unnecessary to make the elastic force of the elastic lifting member 28 to be excessively large for firmly fitting the center portion of the sanitary napkin to the vaginal cavity. Also, since the sanitary napkin can be firmly held with the crotch cloth 19 having large width dimension, displacement of the napkin will not be caused. Therefore, the elastic modulus of the elastic lifting member 28 can be small as about 8.25 (N), 8.91 (N). These are substantially comparable with the longitudinal modulus of the leg band. Accordingly, wringing feeling of the elastic lifting member 28 can be also reduced.

As set forth above, in the present invention, the longitudinal modulus of the elastic lifting member is required to be in a range of ±10% of the longitudinal modulus of the leg band. Also, the longitudinal modulus of the elastic lifting member can be in a range of 7.5 to 10 (N).

As set forth above, since the leg bands are located around the femoral region and relatively large inseam dimension is provided below the crotch, the leg band will never wring into the crotch portion. Also, by the elastic lifting member provided in the back part, the sanitary napkin fitting in the crotch portion can be firmly urged onto the vaginal cavity, liquid absorbing performance can be enhanced to eliminate fear of side leakage. Furthermore, even without providing excessively large elastic force of the elastic lifting member, the napkin can be urged to the crotch portion satisfactorily. Therefore, the sanitary panty according to the present invention can provide good wearing ability without constrictive feeling.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A sanitary panty having a waist band in a waist part, leg bands in leg openings, and a napkin fitting portion in a crotch part, wherein in a three-dimensionally shaped condition as worn, a ratio of a dimension between a center front length from said crotch part to said waist part and a dimension of a total length from one edge of said leg opening to said waist part at a position where the edge of said leg opening is located closest to said waist part, as taking that the center front length is 100, is in a range of 80 to 200 in said total length, an elastic lifting member extending from said crotch part to said waist part is provided in a back part, and an inseam dimension from a center of said crotch part to said leg opening is greater than or equal to 30 mm.

2. A sanitaiy panty having a waist band in a waist part, leg bands in leg openings, and a napkin fitting portion in a crotch part, wherein in a three-dimensionally shaped condition as worn, a ratio of a dimension between a center front length from said crotch part to said waist part and a dimension of a total length from one edge of said leg opening to said waist part at a position where the edge of said leg opening is located closest to said waist part, as taking that the center front length is 100, is in a range of 80 to 200 in said total length, an elastic lifting member extending from said crotch part to said waist part is provided in a back part, and said crotch part is formed with a stretchable cloth which can elastically stretch in back and forth direction, a napkin fitting cloth is provided inside of said crotch part, a front edge and a back edge of said napkin fitting cloth are sewn with said crotch part in a front side sewing portion and in a back side sewing portion, and an intermediate portion thereof is not sewn to said crotch part.

3. A sanitary panty as set forth in claim 2, wherein between said front side sewing portion and said back side sewing portion, a length of said napkin fitting cloth, as taking a free length of said crotch part being 100, is in a range of 110 to 150.

4. A sanitary panty as set forth in claim 2, wherein a latitudinal dimension of said crotch part is in a range of 1.25 to 17.50 times a latitudinal dimension of said napkin fitting cloth.

5. A sanitary panty as set forth in claim 2, wherein a crotch cloth of an stretchable cloth is located in said crotch part, said crotch cloth is sewn with a front part and said back part in said front side sewing portion and in said back side sewing portion, and said front side sewing portion and said back side sewing portion extend to an edge of said leg openings.

6. A sanitary panty as set forth in claim 5, wherein said elastic lifting member is joined to a back edge of said crotch cloth in said back side sewing portion.

7. A sanitary panty as set forth in claim 6, wherein a longitudinal modulus of said elastic lifting member is in a range of ±10% of a longitudinal modulus of said leg band.

8. A sanitary panty as set forth in claim 7, wherein a longitudinal modulus {(contracting force (N)/tensile strain (%))×100} of said elastic lifting member is in a range of 7.5 to 10N.

* * * * *